(12) United States Patent
Rutty

(10) Patent No.: US 7,909,399 B2
(45) Date of Patent: Mar. 22, 2011

(54) BACK SUPPORT FOR SEAT

(76) Inventor: John G. Rutty, Hanover, PA (US)

( * ) Notice: Subject to any disclaimer, the term of this patent is extended or adjusted under 35 U.S.C. 154(b) by 113 days.

(21) Appl. No.: 12/246,125

(22) Filed: Oct. 6, 2008

(65) Prior Publication Data

US 2009/0146475 A1 Jun. 11, 2009

Related U.S. Application Data

(60) Continuation-in-part of application No. 11/266,252, filed on Nov. 4, 2005, now Pat. No. 7,448,682, which is a continuation-in-part of application No. 10/862,577, filed on Jun. 8, 2004, now Pat. No. 6,988,772, which is a division of application No. 10/290,264, filed on Nov. 8, 2002, now Pat. No. 6,793,288.

(51) Int. Cl.
*A47C 7/02* (2006.01)
*A47C 7/54* (2006.01)

(52) U.S. Cl. ........... 297/230.11; 297/411.1; 297/411.23; 297/411.25

(58) Field of Classification Search ............... 297/411.1, 297/411.23, 411.25, 411.36, 411.35, 411.4, 297/411.31; 602/20
See application file for complete search history.

(56) References Cited

U.S. PATENT DOCUMENTS

| | | | |
|---|---|---|---|
| 129,202 | A | 7/1872 | Zachos |
| 1,722,205 | A | 7/1929 | Freund |
| 2,546,790 | A | 3/1951 | Shook |
| 2,602,488 | A | 7/1952 | Conning |
| 2,650,650 | A | 9/1953 | Brown |
| 2,667,913 | A | 2/1954 | Dustin |

(Continued)

OTHER PUBLICATIONS

U.S. Appl. No. 10/266,252, Notice of Allowance mailed Jul. 3, 2008, Advisory Action mailed Apr. 10, 2008, Interview Summary mailed Mar. 14, 2008, Final Office Action mailed Jan. 3, 2008, Office Communication mailed Jul. 30, 2007, Non-Final Office Action mailed Jun. 22, 2007, Restriction/Election mailed May 1, 2007.

(Continued)

*Primary Examiner* — Sarah B McPartlin
(74) *Attorney, Agent, or Firm* — Miles & Stockbridge P.C.; David R. Schaffer, Esq.

(57) ABSTRACT

An orthopedic back support for displacing a person's weight from the lower area of the spine by providing support for the upper torso and for use with a chair or seat having a seat base and a seat back. A flexible fabric cross piece is connected between vertical axillary support members to provide back support. The cross piece may include vertical channels or sleeves at opposite sides to receive and support the vertical members. The entire unit is portable and when in use facilitates unobtrusive intermittent use and easy ingress and egress from the seat to relieve discomfort after long periods of use. A rib band may be attached to the flexible fabric by means of hook and loop fabric strips such as Velcro to form a detachable connection. A hook strip is disposed on the back of the rib band and is adapted to cooperate with a mating soft loop strip on the forward side of the flexible fabric member which supports the user in a seated position by the combined action of the flexible fabric and rib band. Alternatively, the rib band may be used separate from flexible fabric back support in which case the detachable connection is made between the rib band and the seat back. The connections are such that the force of connection is greater in sheer than in tension.

5 Claims, 15 Drawing Sheets

U.S. PATENT DOCUMENTS

| | | |
|---|---|---|
| 2,725,928 A | 12/1955 | Branick |
| 3,004,794 A | 10/1961 | Yerkovich |
| 3,063,752 A | 11/1962 | Moore |
| 3,531,158 A | 9/1970 | Allen |
| 4,022,197 A * | 5/1977 | Castiglia ............ 602/61 |
| 4,487,201 A | 12/1984 | Ciambarella et al. |
| 4,788,969 A | 12/1988 | Thompson |
| 4,834,457 A | 5/1989 | Head |
| 4,898,185 A * | 2/1990 | Fuller ............ 128/876 |
| 4,996,978 A | 3/1991 | Gingras |
| 5,123,427 A * | 6/1992 | Watt et al. ............ 128/876 |
| 5,220,692 A * | 6/1993 | Cox ............ 2/48 |
| 5,224,924 A | 7/1993 | Urso |
| 5,251,957 A | 10/1993 | Lemens |
| 5,333,623 A * | 8/1994 | Fuller ............ 128/875 |
| 5,405,313 A | 4/1995 | Albin |
| 5,462,518 A | 10/1995 | Hatley et al. |
| 5,529,383 A | 6/1996 | Laco |
| 5,533,787 A | 7/1996 | Xiang |
| 5,547,253 A | 8/1996 | Schwartz et al. |
| 5,624,158 A | 4/1997 | Adat et al. |
| 5,651,764 A | 7/1997 | Chiu |
| 5,897,161 A | 4/1999 | Karg |
| 6,015,395 A | 1/2000 | Kautzky |
| 6,125,851 A | 10/2000 | Walker et al. |
| 6,332,232 B1 | 12/2001 | Neal |
| 6,793,288 B2 | 9/2004 | Rutty |
| 6,988,772 B2 | 1/2006 | Rutty |
| 7,448,682 B2 | 11/2008 | Rutty |

OTHER PUBLICATIONS

U.S. Appl. No. 10/862,577, Notice of Allowance mailed Jul. 28, 2005, Non-Final Office Action mailed Oct. 20, 2004.

U.S. Appl. No. 10/290,264, Notice of Allowance mailed May 17, 2004, Interview Summary mailed Feb. 13, 2004, Non-Final Office Action mailed Sep. 22, 2003, Restriction/Election mailed Jul. 14, 2003.

* cited by examiner

BACK SUPPORT FOR SEAT

CROSS REFERENCE TO RELATED APPLICATION

This application is a continuation-in-part of application Ser. No. 11/266,252 filed Nov. 4, 2005, now U.S. Pat. No. 7,448,682 which in turn is a continuation-in-part of application Ser. No. 10/862,577 filed Jun. 8, 2004, now U.S. Pat. No. 6,988,772 which is a divisional of application Ser. No. 10/290,264 filed Nov. 8, 2002, now U.S. Pat. No. 6,793,288, issued May 13, 2004.

BACKGROUND OF THE INVENTION

1. Field of the Invention

This invention is related to the field of back supports, more specifically to back supports for use with a seat which enables a user to conveniently raise himself and stretch to relieve muscle tension.

2. Description of the Prior Art

Lower backaches and back pain are a frequent occurrence in modern-day society and may be attributed to a number of factors. Those who suffer from lower back pain can frequently be recognized by contortions they go through to relieve the stress on their lower back. Doctor's often recommend to their patients that they get off their feet to take the weight of the torso off their lower back. Unfortunately, sitting does not accomplish this. Many people with lower back pain find it necessary to spend a fair amount of time in a seated position. This is especially true for the common business person, who may spend a fair amount of time traveling while in a car or seated behind a desk for a generous portion of the day. This places significant stress on the lower back.

Various back supports are known for relieving painful aches of the lower spinal column or tiring muscles of the lower back. Such back supports are particularly helpful when a person is in a situation that necessitates sitting for a long period, such as when confined in a car or other vehicle or in a plane over a long period. Recent results reveal a cumulative benefit when the back is positioned correctly and supported even for short periods of time.

U.S. Pat. No. 6,125,851 discloses a spinal support system for applying a directed and concentrated force on the sacrum to position the sacrum and pelvis in order to establish a desired spinal posture when a person is in a seated position. To accomplish this force direction, the force is applied from the sacral base level of the seated individual downwardly to a bottom seat surface and across the individual's back.

U.S. Pat. No. 5,529,383 discloses a back support device for retaining a user in a substantially upright position when seated in a chair. The back support comprises a bracket that is attached to the back of a chair and a padded strap that supports the abdomen of the sitting individual.

U.S. Pat. No. 5,624,158 discloses an adjustable backrest for use in a seat, the backrest incorporating a vertical spine member having a lumbar support and upper back support projecting therefrom. Structure is provided for adjusting the curvature of the lumbar support member to fit the curvature of an individual's lower back.

These devices are representative of various approaches that have been taken in an attempt to alleviate back pain. While they all provide some relief in one form or another, such devices suffer from the disadvantage that they fail to alleviate the potentially dangerous weight the upper torso places on the lower back. Further, after long periods of use of a back support, the user needs to be able to conveniently raise himself to stretch and thereafter return to the supported position.

A device designed to partially support the upper torso of an occupant in an automobile is described in U.S. Pat. No. 4,487,201. The back support described therein comprises a wide-band suspension strap that wraps around a user's upper torso region and is supported by the vertical backrest of an automobile seat. Such a device imposes severe limitations on movements of the user, as well as making entry and exit from the automobile cumbersome. Such cumbersome devices do not lend themselves for use by those with active lifestyles or those who find it necessary to make frequent but short automobile trips and are continually moving in and out of an automobile. Intermittent use of the device, whether on long or short automobile trips, requires stopping the car to disengage the strap. While it might be alternatively possible to disengage the strap while operating the automobile, this creates a potentially dangerous situation.

U.S. Pat. No. 4,834,457 discloses another arrangement for supporting the upper torso of a user above a seat by utilizing armpit rests attached to a propping mechanism. A disadvantage of such a device is that it is difficult to adjust in order to fit each unique user and there are no means for providing variable support to the user. Another disadvantage of this device is the poor design of the armpit rests, which can place potentially damaging pressure on nerves extending into the arms of a user.

While the above-identified patents disclose various forms of back supports, none taken singularly, nor in any combination, disclose a back support that supports the upper torso of user for alleviating a portion of a user's weight on the lower back and which may be ergonomically constructed, easily adjusted to fit a user of any size, facilitate unobtrusive intermittent use and easy ingress and egress from a chair and which may be portable and capable of use in a vehicle or in a home environment or any location where there is a suitable chair for the person.

SUMMARY OF THE INVENTION

The aforenoted disadvantages of known back supports are overcome by the present invention which provides an orthopedic back support readily adapted for use with a chair or vehicle seat, such as an automobile, plane, or boat seat, and which can relieve or prevent back discomfort or pain while facilitating unobtrusive intermittent use and easy ingress and egress from a chair or seat to relieve discomfort. In contrast to the majority of prior developed back supports that have little effect on the gravity pressure of the torso on the lower back when an individual is in a seated position, I have developed an invention designed to lift the torso pressure off the lower back with the biomechanical principles of relative distraction/traction. Axillary rests positioned in the axilla or armpit of a user are vertically adjustable to accommodate users of different body heights to lift the upper body to unload the pressure on the lower back, thereby alleviating a degree of pressure on the lower back while sitting that is appropriate for each individual user. Reference is made to my aforenoted applications and patents.

The more pressure put on the axilla, the greater the possibility that the individual can receive potentially harmful pressure on the nerves going into the arms. I have now developed a simpler version of my back support which can be used independently of the type of back support shown in my aforenoted applications and patents or together therewith a slight modification, namely adding a hook-loop fastener, such as Velcro, between the flexible fabric and the back of a rib band. The loop strip attachment is affixed to the front surface of the flexible fabric member for attachment when in use to a hook strip on the rib band. When used independently of the fabric member back support, the soft loop strip attachment is affixed to the seat back.

It is an object of the present invention to provide an economical orthopedic back support that alleviates the weight of an individual's torso on the lower back and corrects tendencies to slump or slouch while facilitating unobtrusive intermittent use.

It is another object of the present invention to provide an orthopedic back support that is adaptable to persons of different sizes.

It is yet another object of the present invention to provide an orthopedic back support that is easily portable which allows the user to intermittently stretch after periods of use.

It is still another object of the present invention to provide a portable orthopedic back support that is economical in construction, easy to use and which allows easy and quick relief from long periods of sitting.

It is still yet another object of the present invention to provide an orthopedic back support that provides a variable or adjustable support to accommodate persons of various sizes as well as the percentage of weight supported and the degree of stress relief provided.

It is still yet another object of the present invention to provide an orthopedic back support utilizing which permits intermittent use and enables a person to conveniently get up and stretch by using rib band and hook-loop releasable attachment.

It is a further object of the present invention to provide an orthopedic back support that does not place harmful and potentially damaging support pressure on the user and permits easy ingress and egress from a chair or seat.

BRIEF DESCRIPTION OF THE DRAWINGS

These objects and the attendant advantages will become readily apparent from the following Detailed Description of the Invention when considered in conjunction with the following drawings wherein like parts are represented by like reference characters throughout the several views.

DETAILED DESCRIPTION OF THE INVENTION

Figure 1:
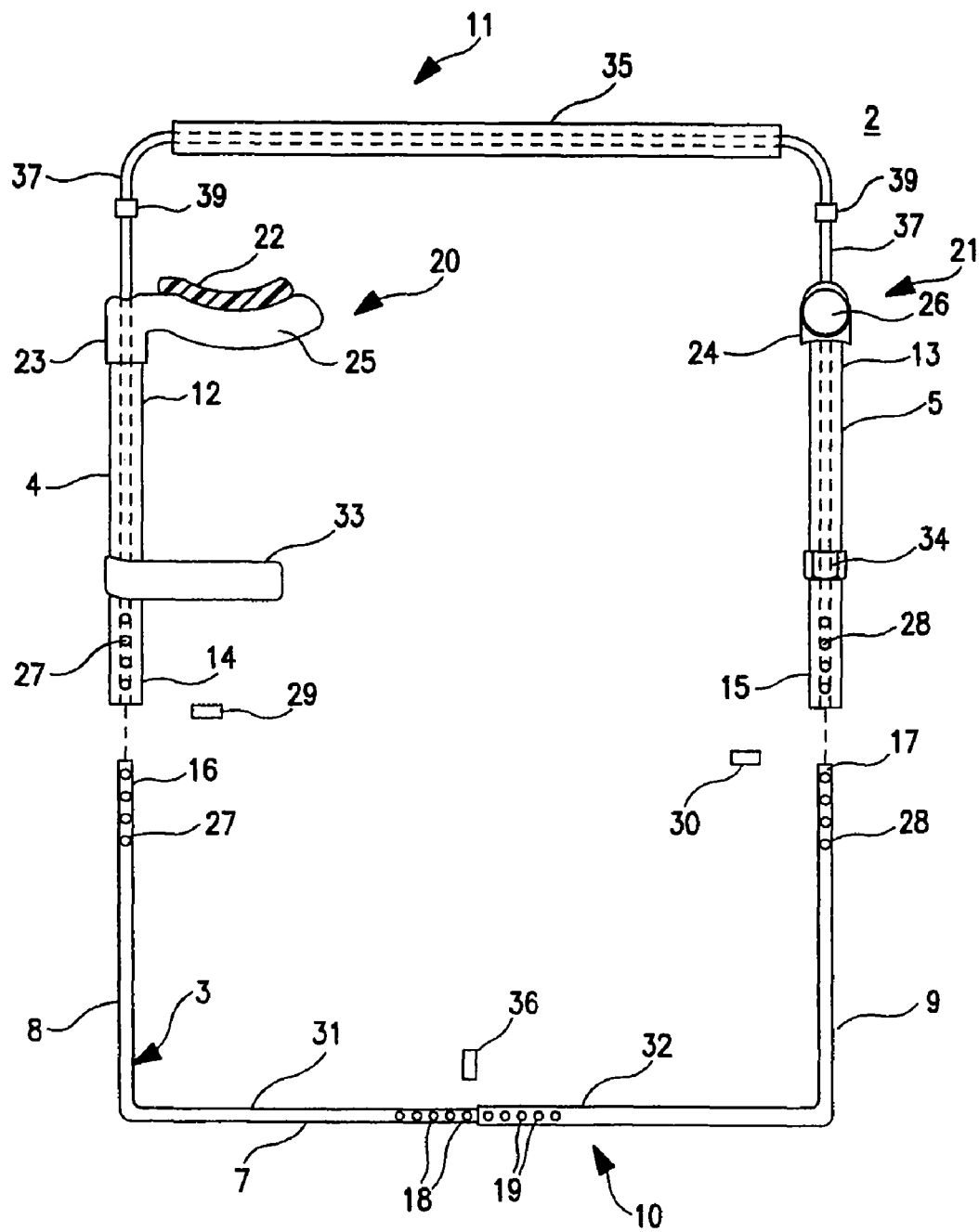
FIG. 1 shows an exploded view of an exemplary embodiment of the present invention.

Referring to FIGS. 1 through 4, an exemplary embodiment of an orthopedic back support 2 of the present invention for use with a chair (FIG. 2) or vehicle seat (FIG. 4) is illustrated. As shown in FIG. 1, support 10 includes a back a back support frame 3 comprising a pair of side members 4, 5, a lower support 10, and an upper support 11.

Side members 4, 5 are substantially rigid, preferably tubular structures that are vertically disposable against a substantially planar surface, such as seat back 51 of a seat or chair 50. Members 4, 5 have a substantially hollow cylindrical section adapted to receive the extending arms 8, 9 of lower support 10. Members 4, 5 and support 10 have sufficient structural support for sustaining a portion of weight from an individual's upper body. In the exemplary embodiment, each member 4, 5 measures between approximately 8¼ inches and 14 inches in length and has a 1 inch diameter. However, it should be appreciated that in alternative embodiments, any dimensions providing the required structural support may be utilized. It should also be appreciated that the members are not restricted to a cylindrical or tubular shape and may vary in alternative embodiments.

Referring more particularly to FIG. 1, it will be seen that each member 4, 5 has a corresponding first upper end 12, 13 and a corresponding second lower end 14, 15 wherein each first end 12, 13 terminates in an axillary rest 20, 21 that extends outwardly from ends 12, 13, respectively, and at a substantially right angle therefrom.

Each axillary rest 20, 21 is L-shape having a short leg 23, 24 and a long leg 25, 26, respectively. It is preferable that each axillary rest 20, 21 is a single element.

Short legs 23, 24 are disposed on respective members 4, 5 at first upper ends 12, 13, respectively. Rests 20, 21 fit tightly to members 4, 5. However, members 4, 5 are allowed to rotate by design, as well be explained soon hereafter, thereby permitting easy entry and exit from back support 2, as well as intermittent use. The swiveling motion also allows variable alteration of forces from side to side to enhance adjustability of back support 2. If a user experiences temporary excess axillary pressure or arm nerve irritation, axillary rests 20, 21 can be easily rotated from the forward engaged position to an unobtrusive position flush to seatback 51, 55 in FIGS. 2 and 4, respectively.

Long axillary rest legs 25, 26 extend about 7½ inches relatively perpendicular to members 4, 5 and are curved to accommodate the axilla. The dimensions of long legs 25, 26 may vary in alternative embodiments. A soft padding 22 of rubber, gel, or other material may be wrapped around or applied to the top surface of each long leg 25, 26 to alleviate discomfort in the axilla or to alter the girth for a customized fit and support. However, it should be appreciated that such padding is a desirable feature for comfort and is not a requirement of the invention.

As shown in the exemplary embodiment, each axillary rest 20, 21 may have an upward curvature having a radius, for example of 8 inches, much like the curvature at the top of a typical crutch. The curvature of long legs 25, 26 provide additional support and comfort when placed in the axilla. This optimal design allows more contact and support on the posterior altissimo dorsi muscle as well as some anterior support on the pectorals muscle. Such contact and support decreases forces in the central axilla that would tend to irritate the nerves that enervate the arms. This design of the axillary rests allows the user increased distraction forces to unload pressure on the lower back while minimizing the adverse potential of brachial plexis nerve irritation.

Lower support 10 comprises lower support members 8, 9, which are joined by a lateral cross member 7 adapted to rest on horizontal seat portion 52 of seat 50.

Figure 3:
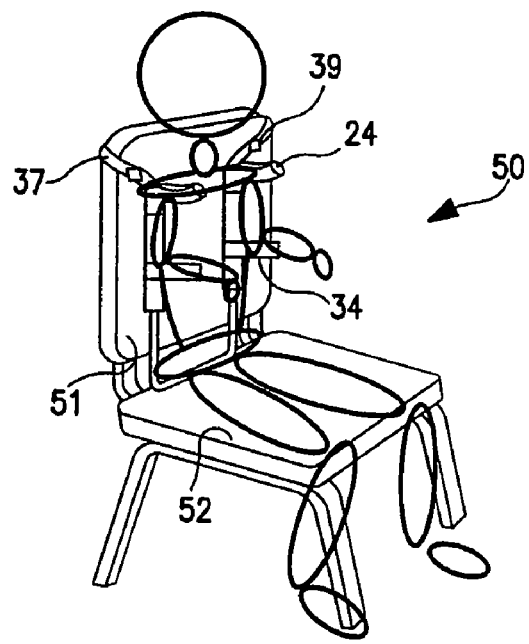
FIG. 3 shows a perspective view of the exemplary embodiment of FIG. 1 and the manner in which the invention is used.

In operation as seen in FIG. 3, the user positions themselves in a seated position. Lower and upper supports 10, 11, respectively are joined together and placed behind the back of a user, with axillary rests 20, 21 placed in each axilla. Lower supporting cross member 7 is adjustably positioned on a seat surface 52 so as to support a portion of weight of a user's torso by virtue of cross member 7 pushing directly against seat surface 52, thereby bypassing the normal transfer of weight through the lower back.

U-shape support 7, 8, 9 may be fabricated in separate pieces telescopingly joined together in a conventional manner. Upper ends 16, 17 are received by second ends 14, 15 of joining members 4, 5, respectively. To this end, the diameter of end 16, 17 is slightly less than the diameter of each second end 14, 15 of joining members 4, 5 so that members 4, 5 may telescopingly accept ends 16, 17. This establishes a telescoping engagement between members 4, 5 and elements 8, 9, respectively of the lower U-shape support to enable vertical adjustment of the position of axillary rests 20, 21 relative to seat surface 52. While the drawings show members 4, 5 receiving ends 16, 17 of elements 8, 9, it should also be appreciated that the members may be received in a reverse relationship. As shown in FIG. 1, cross member 7 may likewise be fabricated such that one side 31 telescopingly fits in another side 32 to adjust for the width of a user. For example, by aligning a peg hole 18 of side 31 with a peg hole 19 of side 32, a pin 36 may be inserted therethrough to lock each side 31, 32 together, thereby adjusting the lateral width of cross member 7 accordingly. Alternatively, the U-shape support element may advantageously be a one-piece rigid structure with the lower support element adapted to be disposed against a seat surface.

To adjust or set the vertical position of rests 20, 21 relative to seat surface 52, U-shape element 7, 8, 9 is preferably an adjustable support to fit the frame to users of different sizes. As shown in FIG. 1, a plurality of vertically spaced peg holes 27, 28 span a portion of each end 14, 15, for receiving a pin 29, 30. Holes 27, 28, in cooperation with pin 29, 30 provide adjustments for an optional forearm rest 33, 34. The vertical positions of axillary rests 20, 21 can be adjusted by sliding each member 4, 5 along ends 16, 17 until the desired height is achieved. The pin or peg 29, 30 is then placed into one of the plurality of peg holes 27, 28 so that receiving ends 16, 17 rest against pin 29, 30 within members 4, 5, respectively. Such an engagement permits members 4, 5 to be vertically adjustable and axillary rests 20, 21 may be maintained at a comfortable position in the axilla of the user. Furthermore, members 4, 5 may rotate on receiving ends 16, 17 so that rests 20, 21 may be swiveled to a comfortable position or for easy ingress and egress from support 2. Side members 4, 5 may free rotate up to 189 degrees on ends 16, 17 of U-shape support member 7, 8, 9. Axillary rests 20, 21 and each side member 4, 5 may be fabricated as a single piece, such as by extrusion from a mold. A friction washer or snugging gasket are between the inner walls of members 4, 5 and receiving ends 16, 17 to oppose the vertical separation of members 4, 5 from ends 16, 17 but permit swiveling thereon. It should be appreciated that a telescoping peg hole arrangement may be provided in cross member 7, connecting left side 31 and right side 32 by passing pin 36 therethrough to adjust for the width of the user.

The optional forearm rest 33, 34 for the elbow or forearm may bear additional weight helping to relieve the load on the lower back. While the present embodiment shows each forearm rest 33, 34 having a sleeve around members 4, 5 which rests on pin 29, 30 for support, it should be appreciated that in alternative embodiments, forearm rests may be engaged with members 4, 5 through the use of pegs, pins, grooves, sleeves or any other means for interlocking so long as height adjustments are easily obtainable for forearm rests 33, 34 and they are free to swivel.

Figure 2:
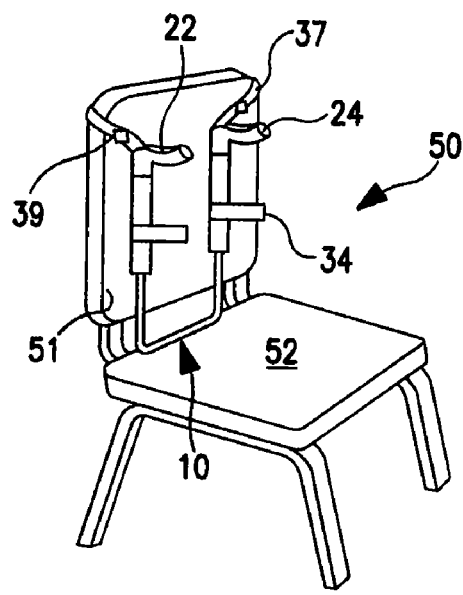
FIG. 2 shows a perspective view of the exemplary embodiment of FIG. 1 in combination with a seat having a seat back.
Figure 20:
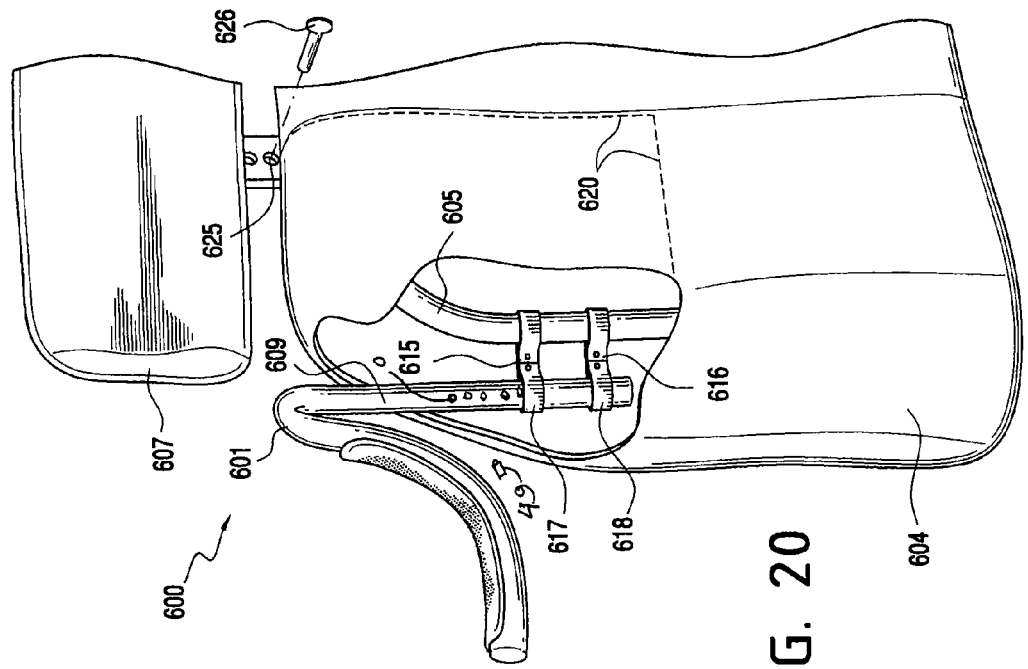
FIG. 20 shows the embodiment illustrated in FIG. 19 with part of the seat cut away to show internal parts.
Figure 19:
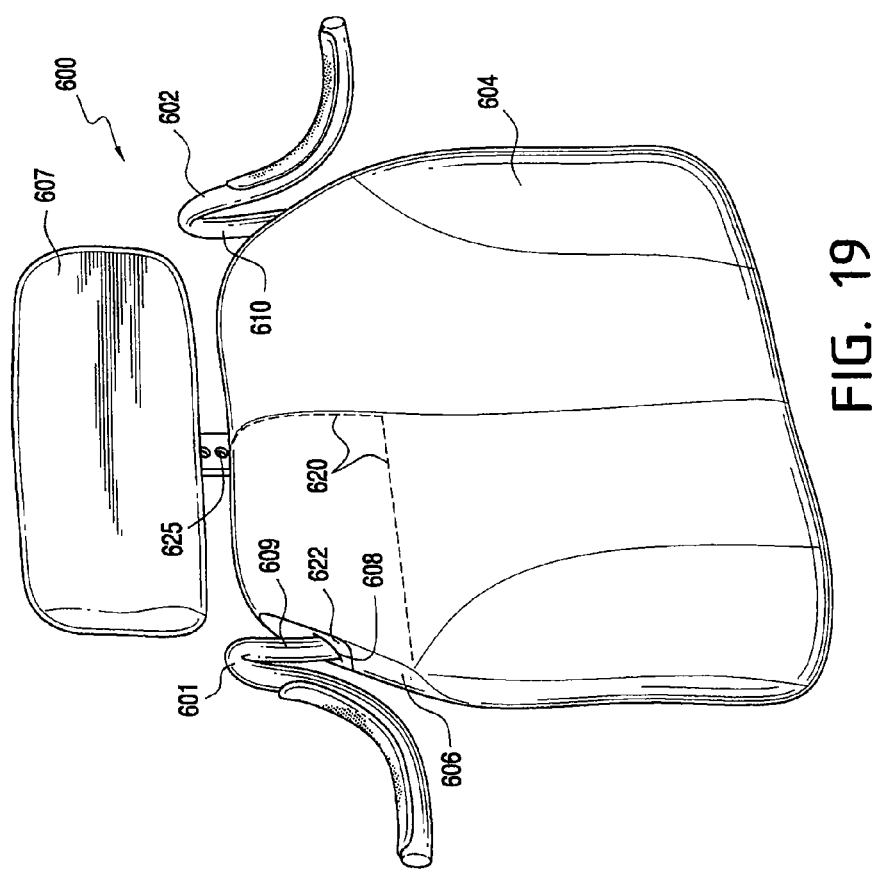
FIG. 19 shows an alternative embodiment of the invention for use in a vehicle seat.

In accordance with the present embodiment of the invention, upper support 11 comprises a rod 35 through which passes a flexible strap 37 which is adjustable in length by the use of a clasping mechanism 39. Clasping mechanism 39 may include, but should not be limited to, buckles, snaps, or other clasping means. Strap 37 is joined at each end to axillary rests 20, 21, providing tensioned support by pulling substantially upward on axillary rests 20, 21. Rod 35, if acting as a guide and support for strap 29, is disposable behind seat back 51 or a headrest to further enable the rests 20, 21 to support and displace a portion of weight from the torso against the top or back of seat back 51 and advantageously reduce the size and strength of the materials otherwise necessary to support heavy weight, thereby increasing its capacity for use as a mobile back support. Alternatively, the rod 35 may be solid having the flexible strap attached to each end of the rod, or the rod may be dispensed with and the strap 37 is positioned over and behind the back rest as shown in FIGS. 2 and 3. When used, rod 35 has a length that approaches or is substantially equal to the spacing of the vertical support member 4-5 such that the opposite ends of the flexible members are in axial alignment with the vertical support members 4 and 5. When the rod is dispensed with, the strap should be of sufficient strength to provide reliable support for the body when it is extended around the seat back. It should further be appreciated that upper support 11 is optional, and that while it is useful to provide symmetrical support to members 4 and 5 and axillary rests 20, 21 for certain seat backs, some seats as shown in FIGS. 19 and 20 will not require the additional support from a location above the axillary rests.

Figure 4:
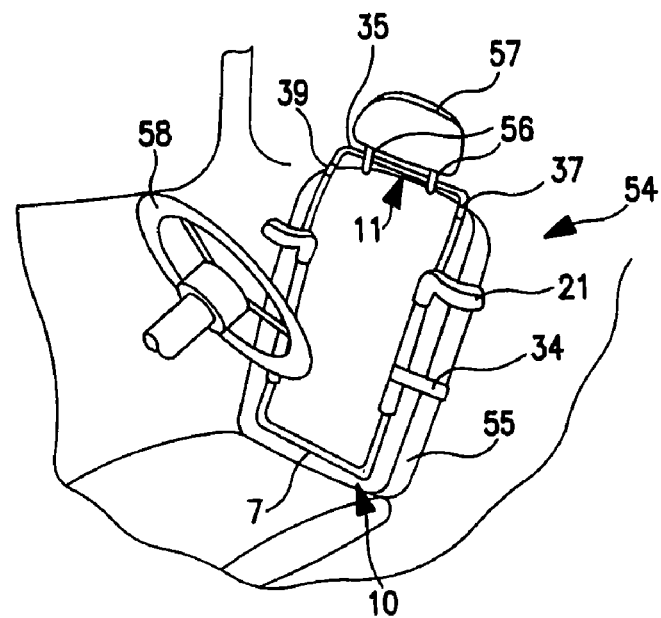
FIG. 4 shows a perspective view of the exemplary embodiment of FIG. 1 in combination with a seat of an automobile with axillary rests turned outward and flush against the seat back.

FIG. 4 shows a present exemplary embodiment of back support 2 used with a seat 54 of a vehicle such as an automobile. It should be readily apparent that support 2 may be used with seats of other vehicles such as boats, planes, or the like. Upper support 11 includes rod 30 disposed behind posts/supports 56 of headrest 57 of seat 54, with strap 37 extending over the top of seat back 55 and attached to axillary rests 20, 21. Rod 30 displaces a portion of weight from the user's torso directly against headrest supports 56 and maintains the straps 37 in substantial axial alignment with the vertical support members 4 and 5 or more clearly shown in FIG. 1. Axillary rests 20, 21 are shown swiveled outward and substantially flush to the surface of seat back 55, which facilitates easy movement into or out of seat 54 normally constrained by steering wheel 58 of the automobile. It should be appreciated that although FIG. 4 depicts the back support frame 2 having a lower support 10, it is not required.

Figure 5:
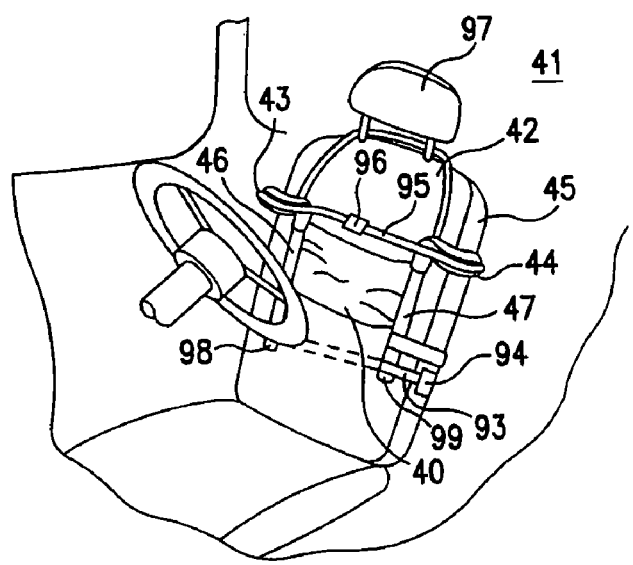
FIG. 5 shows a perspective view of an alternative exemplary embodiment of the present invention having an optional flexible sheet material for lateral support.

While the preferred embodiment has been described herein having a combination of a lower support and an upper support, it should be appreciated that other exemplary embodiments may independently use either a lower support or an upper support. For example, an alternative embodiment of a back support 41 having only an upper support 42 is illustrated in FIG. 5. Support for the lower back is displaced to axillary rests 43, 44 and then to upper support 42, which extends behind headrest 97. Because, no lower support is provided, an optional flexible sheet material 40 extended between side members 46, 47 help to increase the lateral stability of back support 41 to hold side members 46, 47 in proper alignment with the torso of a user. In an alternative embodiment, this flexible material may also be used to support the axillary rests with the use of pockets or sleeves into which the side members would fit as shown, for example, in FIGS. 17 and 18. The upper support would attach to the flexible material and as a result, the lower support is unnecessary. Referring again to the present embodiment, material 40 may be a rattan, rubber, canvas, nylon, or any other durable, flexible sheet or woven material. Also shown in this embodiment is an optional stability strap 93 that is attached to lower end 98 of member 46, extends behind seat back 45, and attached at its opposite end to lower end 99 of member 47. With the absence of a lower support, strap 93 provides added stability and alignment to back support 41 when pulled taut by buckle 94, or other means for adjusting strap 93. An optional chest strap 95 is attached at one end to axillary rest 43 and attached at the opposite end to axillary rest 44. A sitting individual may be harnessed by chest strap 95 by extending it over the upper torso of a sitting individual. Chest strap 95 may include an adjustable, quick release buckle, or other fastening means, to make adjustments for individuals and to maintain the quick ingress and egress characteristics of the invention. When taut, chest strap 95 corrects tendencies to slump or slouch.

Figure 6:
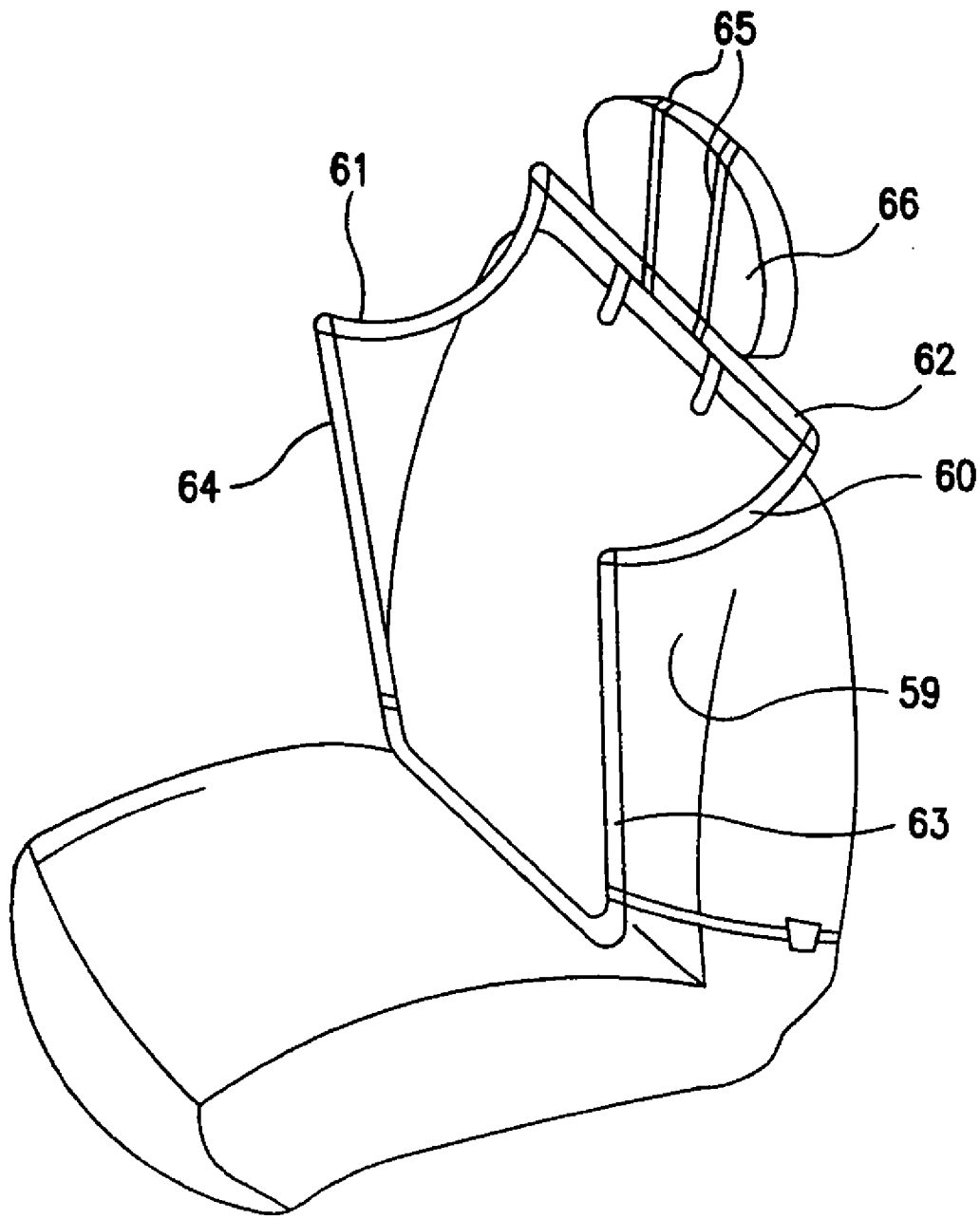
FIG. 6 shows a perspective view of an alternative embodiment of the present invention having a flexible strap for placement in the axilla.

FIG. 6 shows an alternative embodiment having axillary rests 60, 61 comprising flexible straps extending between the ends of rod 62 and rigid members 63, 64, respectively. Cross piece 7 at the bottom of rods 63, 64 and connected thereto at the lower end rests on the horizontal seat cushion to support the weight of the torso and relieve pressure on the back. The position of members 63, 64 is shown pivoted forward from seatback 59. When in operation, straps 60, 61 are placed under each axilla of an individual to provide support. Harness 65 extending upward from rod 35 is secured to headrest 66 to provide both lateral and upright support to straps 60, 61, and thus to the torso of a user. Adjustment of the length of straps 60, 61 may be provided using a buckle, snap, or other mechanism suitable for adjustment. Adjustments of the height and space of rigid members 63, 64 or adjustments to harness 65 on headrest 66 can provide proper distribution of support to the axilla. To this end, rods 63, 64 and cross piece 7 may be telescoping members as shown in FIG. 1. Harness 65 may be positioned behind the two headrest bars that adjustably support the headrest as shown in FIG. 5.

Figure 7:
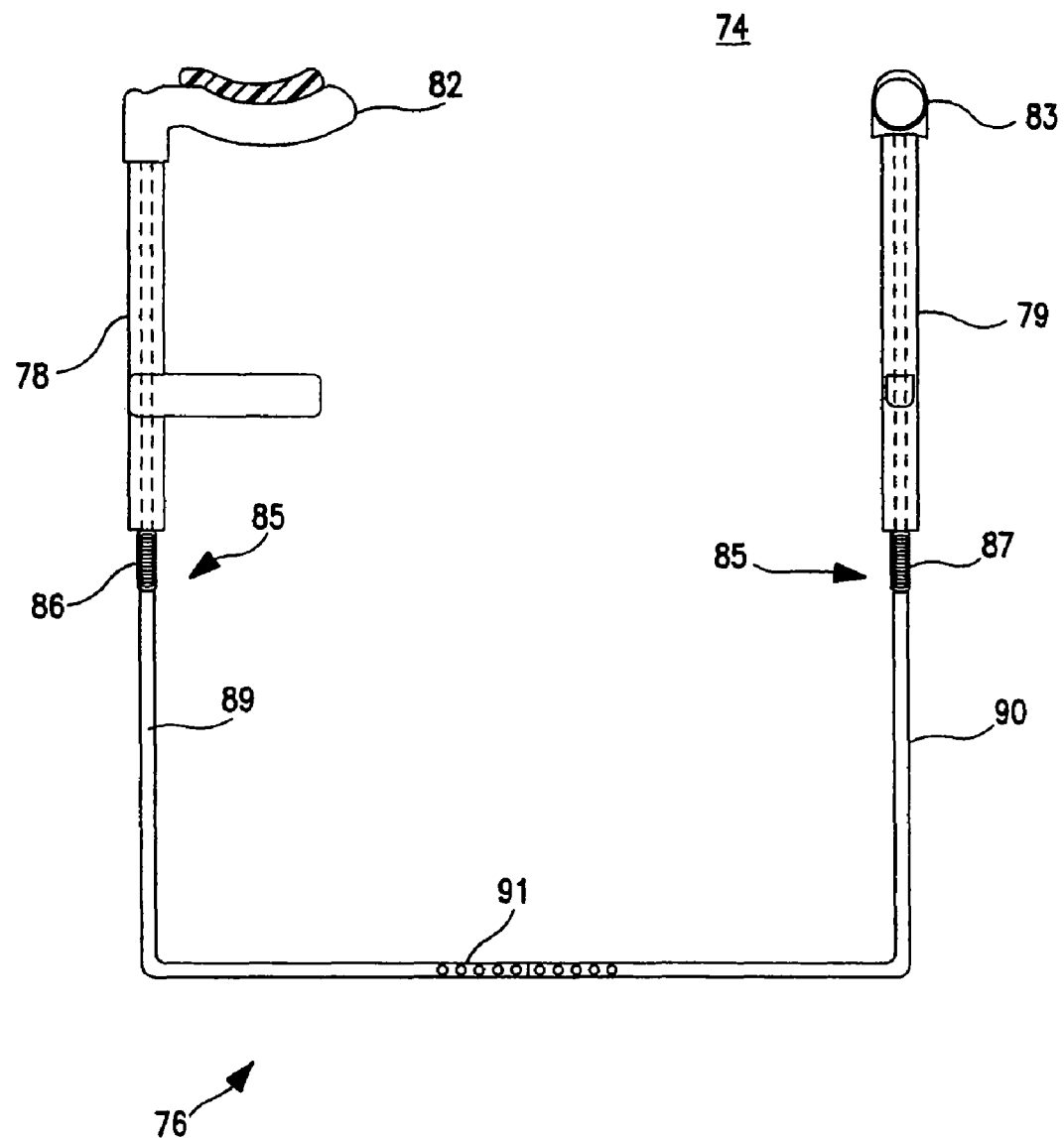
FIG. 7 shows an exploded view of an alternative embodiment of the present invention using variable compression support.

In an alternative embodiment shown in FIG. 7, a back support frame 74 has only a lower support 76 comprising elements 89, 90, 91. In this embodiment, back support 74 provides variable support that raises and lowers the relative height of side members 78, 80 in response to the weight displaced from axillary rests 82, 83 when an upper support is not implemented. A compression support 85 may be varied using springs 86, 87 having an adjustable compression force or length as known by one familiar in the art. Springs 86, 87 fit internally at each end of the U-shaped support element 89, 90 and extend up into side members 78, 80. By this arrangement, the weight of a user's torso on each axillary rest 82, 83 is counteracted by each spring 86, 87, thereby lessening the weight of the torso on the lower back.

Figure 8:
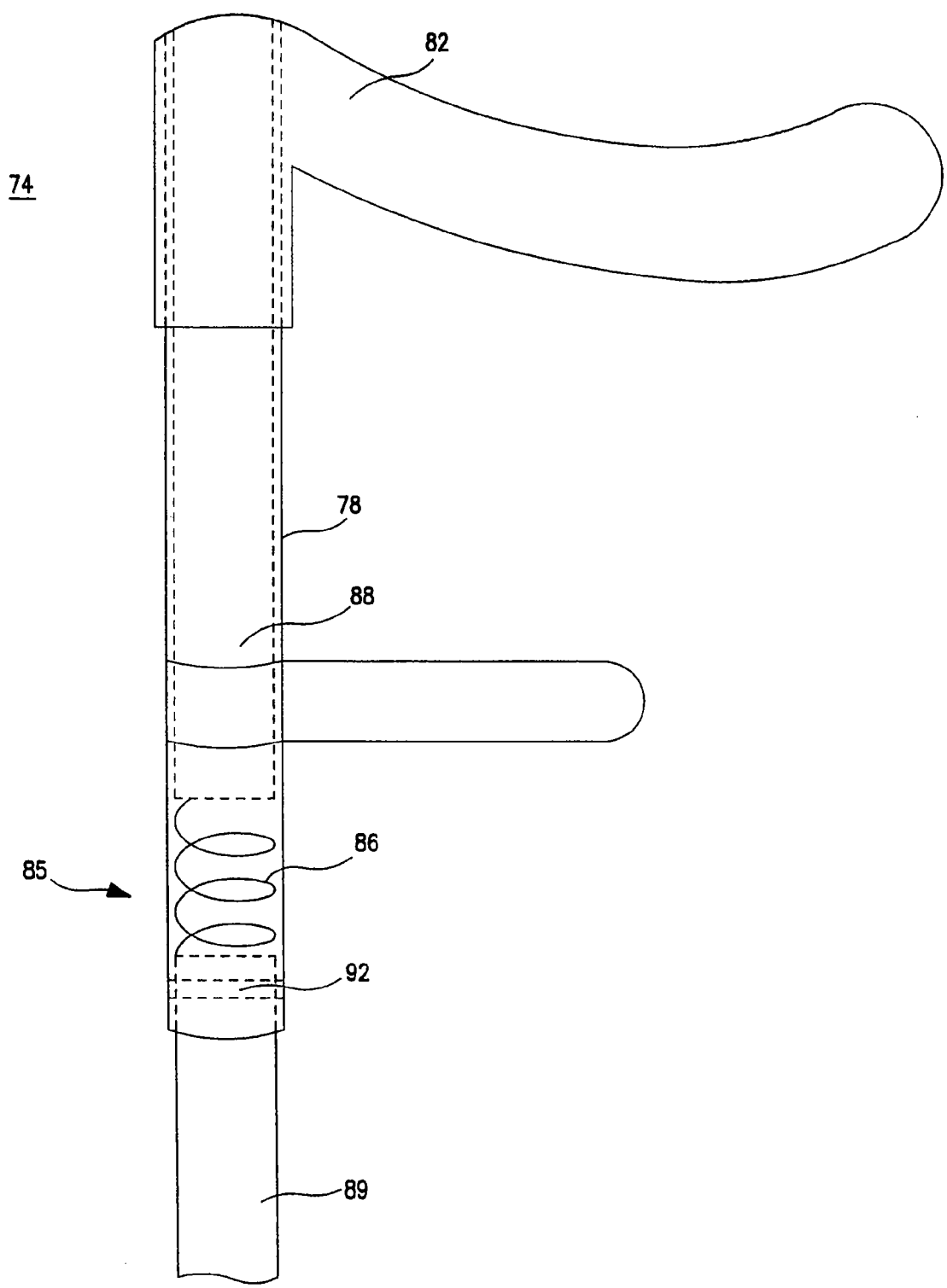
FIG. 8 shows a detail view of the variable compression support of FIG. 7.

FIG. 8 shows a detail view of left compression support 85 comprised of spring 86. A plug 88 extending up into member 78 to axillary rest 82 would compress spring 86 under the weight of an individual using back support frame 74. Plug 88 transfers the compression force from axillary rest 82 to spring 86. The end of U-shape support element 89 holds the compression force at the lower end of spring 86. A snugging gasket 92 prevents element 89 from disengaging from member 78 at a time when there are no compression forces. Also, gasket 92 maintains a snug fit between member 78 and element 89. A relatively heavy force would produce a small compression of spring 86, thereby creating an opposite, upward force to carry a percentage of the weight of a user's torso that would normally be transferred to the lower back. It should be appreciated that in alternative embodiments, plug 88 may not extend upward through side member 78 to axilla rest 82 and instead may be held firmly at an intermediate position within side member 78. It should also be appreciated that a pin or other stopper mechanism may be placed at an intermediate position in side member 78 for transferring compression forces from axilla rest 82 to spring 86.

Figure 9:
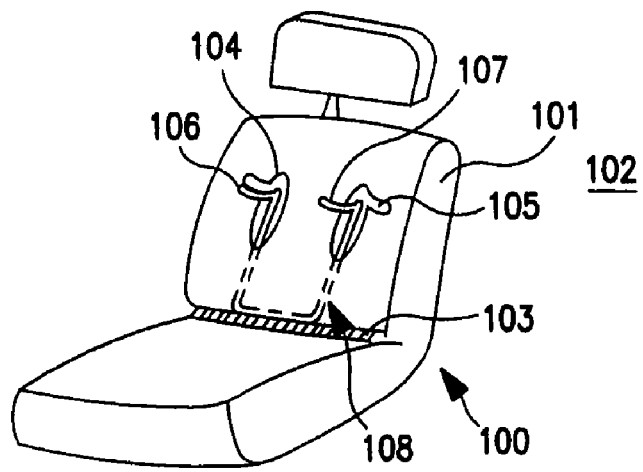
FIG. 9 shows a perspective view of an exemplary embodiment of the present invention having an internally mounted back support.
Figure 10:
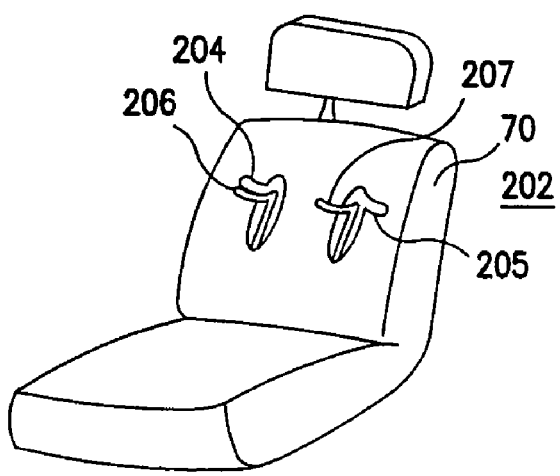
FIG. 10 shows a perspective view of an alternative exemplary embodiment of the present invention having an internally mounted back support.

FIGS. 9, 10, 19 and 20 illustrate exemplary embodiments of a seat mounted back support 102 202. In FIG. 9, the back support 102 includes a lower cross support 108 mounted within a seat back 101 of a seat 100. Seat back 101 has axillary rest openings 104, 105 through which axillary rests 106, 107 extend. Openings 104, 105 are preferably sized and shaped to envelope rests 106, 107 when swiveled for periods of non-use, so as to provide a flush surface to seat back 101. To this end, seat back 101 may include depressed areas in the shape of the axillary rests. Lower support 108 is conveniently supported on a cross beam 103 of seat 100.

FIGS. 10-13 illustrate an alternative embodiment of an internally mounted back support 202.

In the embodiment shown in FIGS. 10-13, seat back support 202 has mounted therein, at the location of openings 204, 205, a pair of supporting plates 212. Each plate includes several pairs of apertures 214, 215; 216, 217; 218, and 219 left, center, right for engaging axillary rests 206, 207 and providing height and width adjustments thereto.

Supporting plates 212 have a substantially planar surface that is internally mounted in seat back 72 of seat 70. Attachment of plates 212 to seat back 72 may be by bolting, welding or other means and will vary according to the internal structure of seat 70. While a universal location may be chosen because of the ability for height adjustments, plates 212 may also be custom fitted. To this end, factors in determining the location of adjustment plate 212 on seat back 72 include the stature of the individual that is being fitted for back support 202, and the type of seat 70. It should be appreciated that in alternative embodiments, support for axillary rests 206, 207 is not limited to adjustment plates 212 as described herein, but any support for supporting the axillary rests to the backrest may be provided, so long as the supporting means permits the axillary rests to swivel against the seat so as to permit its normal use by an occupant not requiring back support.

Figure 11:
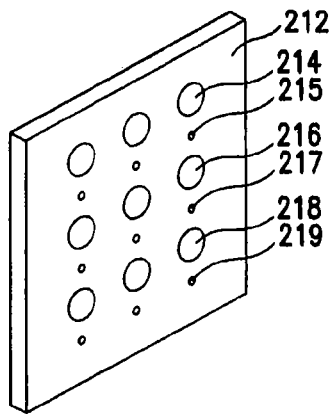
FIG. 11 shows a perspective view of a supporting plate of the alternative embodiment of FIG. 10.
Figure 12:
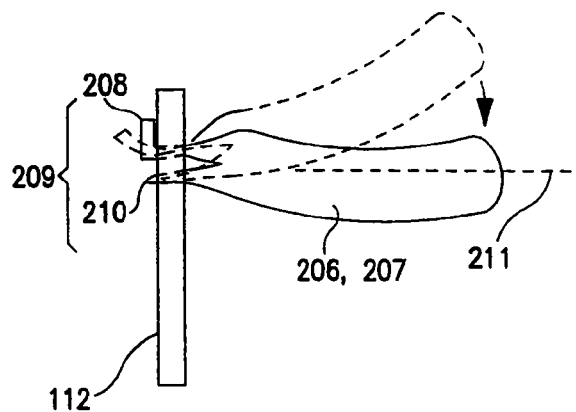
FIG. 12 shows a side view of an axillary rest engaged with a supporting plate in the alternative embodiment of FIG. 10.

Each axillary rest 206, 207 is bifurcated at one end to form a fastening component 209 by cooperation with the openings in associated with support plate 212. As shown in FIG. 11, the bifurcated ends of rest 206, 207 terminate in a hook 208 and a guide pin 210 adapted to pass through a selected pair of openings such as 214, 215.

Figure 13:
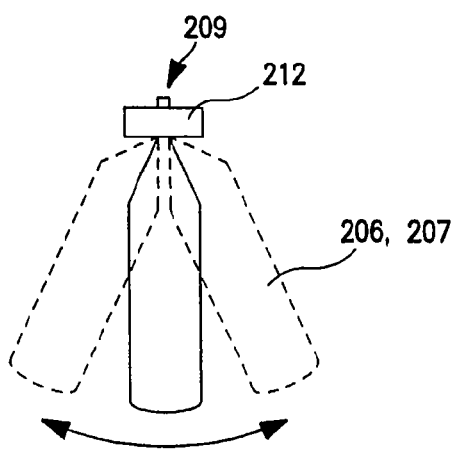
FIG. 13 shows a top view of an axillary rest engaged with a supporting plate in the alternative embodiment of FIG. 10.

The plurality of vertical sets of apertures 214, 215; 216, 217; and 218, 219 at positions of left, center, and right on adjustment plate 212 provide multiple adjustments for height and width positioning of axillary rests 206, 207, enabling back support 202 to adjust to users of a variety of statures. Apertures 214, 216 and 218, are large compared to the cooperative apertures or openings of 215, 217, 219. Each set of apertures has a first, larger orifice, corresponding to apertures 214, 216, 218, for receiving hook 208 and a second aperture, corresponding to apertures 215, 217, 219 for receiving the guide pin 210. The diameter of the large size apertures 214, 216, 218 must be large enough to allow hook 208 to pass through when inserted. Upon insertion, rest 206, 207 is held at an angle, as shown by the dashed line to allow hook 208 to pass through to the backside of plate 212. As rest 206, 207 is moved downward (as shown by the arrow in FIG. 12) to an operational, substantially horizontal position, guide pin 210 engages the smaller aperture of the set. Concurrently, hook 208 becomes engaged with the larger orifice, holding axillary rest 206, 207 to adjustment plate 112. Hook 208 and guide pin 210 when engaged in their respective, associated apertures, prevent axillary rest 206, 207 from collapsing downward under the weight of a user's torso. The double engagement of hook 208 and guide pin 210 also prevent axillary rest 206, 207 from turning along the lengthwise central axis 211 of axillary rest 206, 207 so that hook 208 may stay in proper alignment. Such an engagement, as well as the bifurcated shape of the end of axillary rest 206, 207, permits axillary rest 206, 207 to swivel horizontally as seen in FIG. 13 for easy entry and exit, or intermittent use. Rests 206, 207 can be easily disengaged and removed by reversing the above engagement procedure, whereby rests 206, 207 would be moved upward and out of the associated apertures. It should be appreciated that in alternative embodiments, an alternative fastening component may be used to engage the bifurcated end of axillary rest 206, 207 with supporting means 212. However, such a fastening component should permit the axillary rest to swivel horizontally in the manner previously described. It should also be appreciated that apertures 214, 215; 216, 217; 218, 219; are not limited to the positions of left, center, and right and may have more positions to provide for more horizontal adjustments. Similarly, there may be more than the three sets of apertures 214, 215; 216, 217; 218, 219; to also provide for more vertical adjustments.

Figure 14:
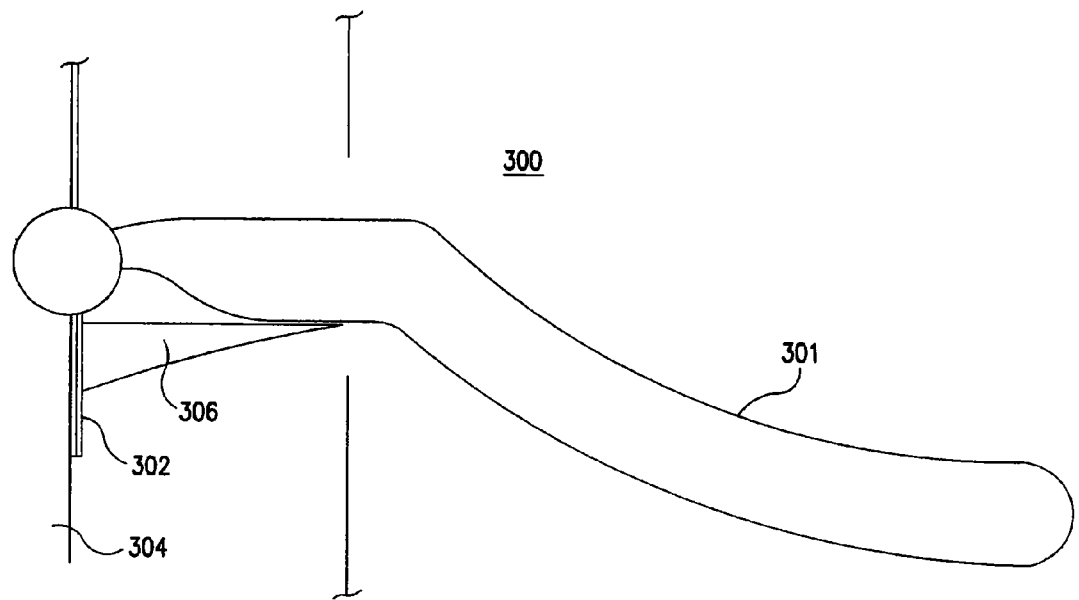
FIG. 14 shows a side view of an alternative exemplary embodiment of the present invention having an internally mounted back support.
Figure 15:
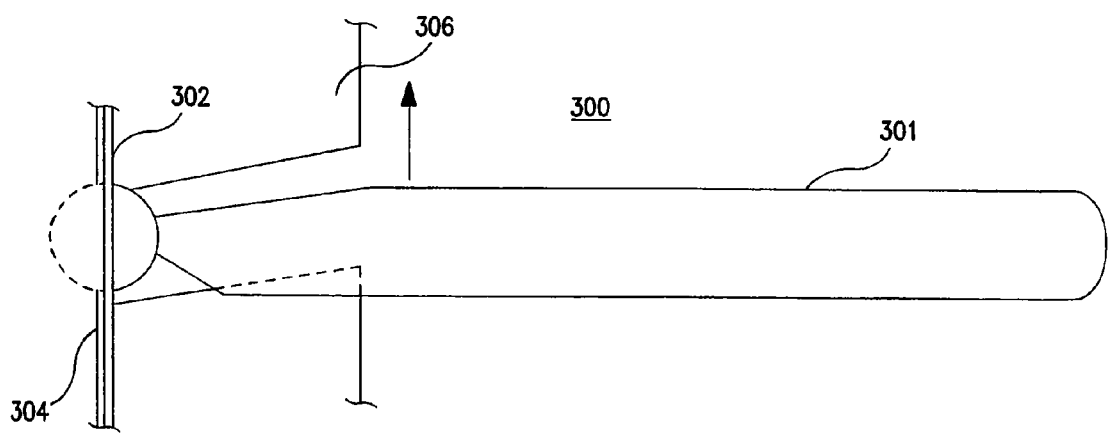
FIG. 15 shows a top view of the alternative embodiment of FIG. 14.

FIGS. 14 and 15 show an alternative exemplary embodiment of an internally mounted back support 300. Referring to FIG. 14, axillary rest 301 is mounted to a moveable plate 302 attached to seat frame 304. In operation, support 306 provides upward support for holding the force exerted downward in rest 301 from a user's torso. A side motion, as indicated in FIG. 15, would be required to put the rest in an unsupported position, allowing a downward vertical rotation to place rest 300 into a recessed opening in seat back 308 when not in use.

Figure 16:
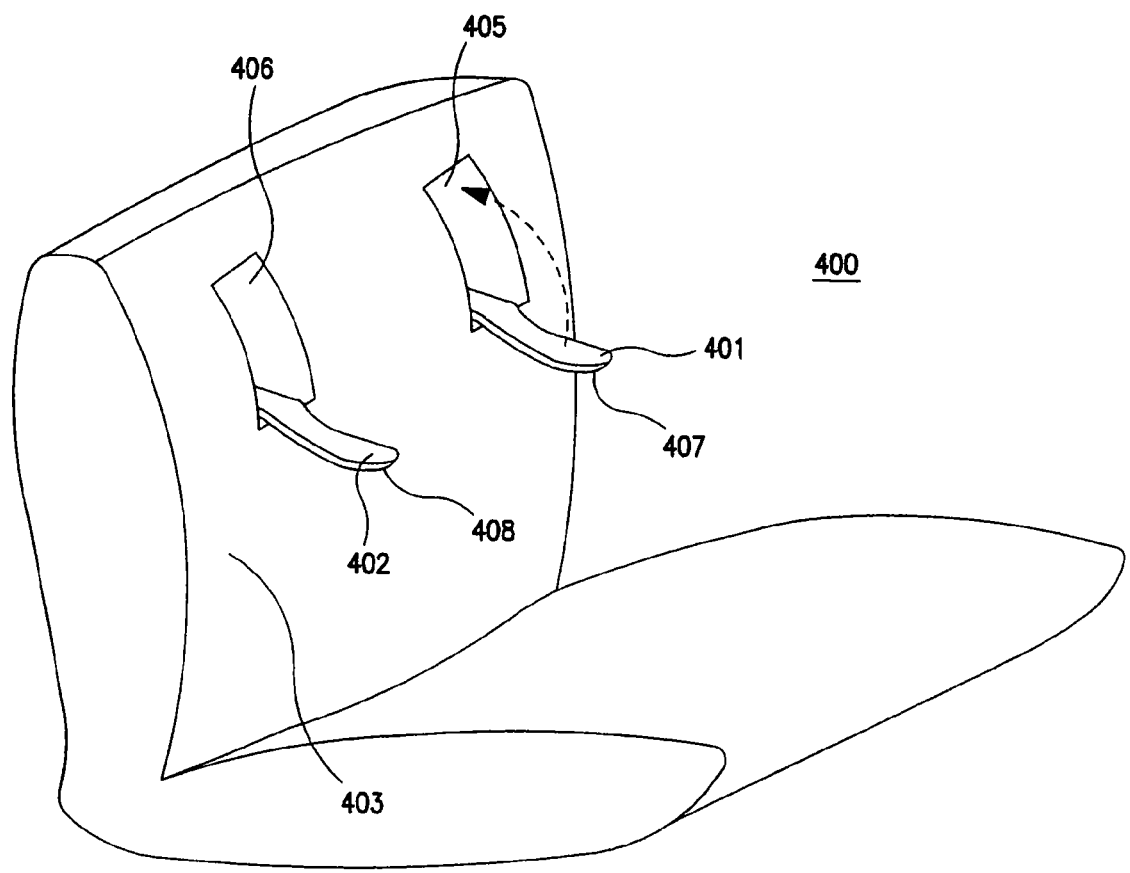
FIG. 16 shows a perspective view of an alternative exemplary embodiment of the present invention having a back support internally mounted in an upholstered seat.

FIG. 16 shows an alternative exemplary embodiment of an internally mounted back support 400. With upward rotation as indicated by the arrow in the figure, the side motion in the aforementioned embodiment would not be required. Rests 401, 402 could be pivoted into recesses 405, 406 to be flush with seat back surface 403 when not supporting the user. Bottom surfaces 407, 408 of rests 401, 402 may be fabricated to match seat back 403 when pivoted into recesses 405, 406, respectively.

Figure 21:
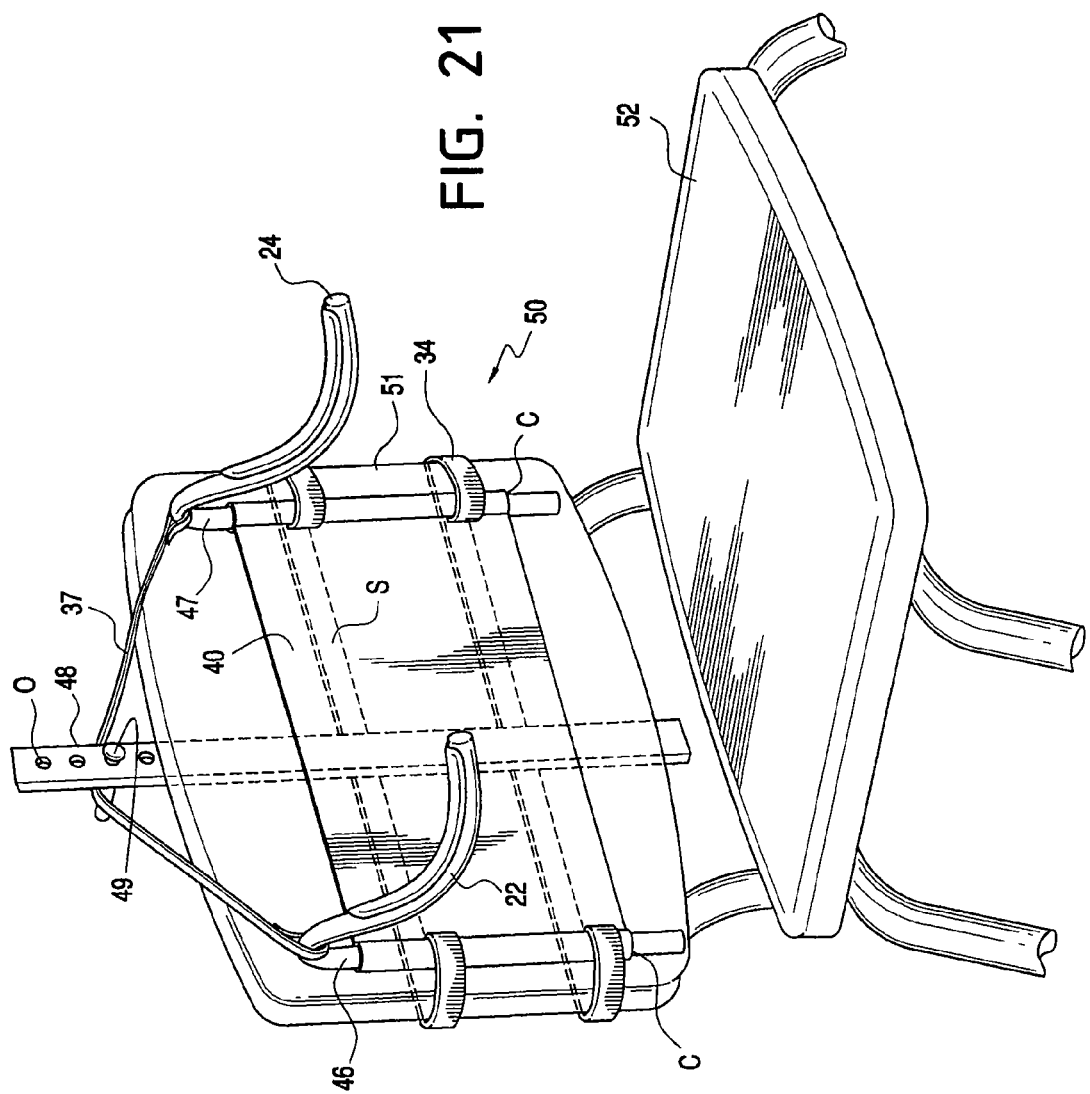
FIG. 21 shows an alternative embodiment of the invention for use with seats having no head rest.

Some situations arise where a person suffering from lower back pain may be forced to sit in situations wherein the only chair available has a low back support, but no head rest, such as a folding chair used in an auditorium lecture or bridge table. In such situations, it may not be possible to position a flexible supporting strap behind the seat back. FIG. 21 illustrates an embodiment which overcomes this problem.

Referring to FIG. 21, there is shown a chair 50 which may be of the folding type having a back 51 and seat 52. The orthopedic back support includes left and right axillary members 22, 24, each comprising a vertical arm member and extending axillary rests. A back fabric support 40 is connected between the axillary members. A vertical support rod 48 includes a hook, pin, peg, or other transverse supporting member 49 adapted to support an upper flexible cross strap 37 connected at opposite ends to the left and right axillary members. A series of vertically spaced peg holes or openings O are provided in rod 48 to allow for vertical adjustment of the axillary members 22, 24 to accommodate users of the back support. In use, a peg 49 is placed in the peg hole O which provides the most comfortable position for the user. A lower anchor strap 34 is adapted to be positioned behind the chair back 51 and over the lower end of vertical support rod 48 to anchor the lower end of rod 48 and prevent the lower end of rod 48 from tipping or swinging outward away from the back of the chair back 51 when the user's weight is placed on the auxiliary members 22, 24. Axillary members 23, 24 are conveniently supported in the vertical channels or sleeves or through cylindrical openings formed at each side of back fabric support 40. Sleeves C are conveniently formed by folding an edge of the fabric over itself and stitching the fold over to main portion of the fabric. The through openings or channels receive the vertical arm 46, 47 of the axillary members. If desired, a middle strap 9 may also be provided for greater stability. The upper strap 37 may be looped at their ends around the axillary members. The ends of the straps 34 and 40 preferably include hook and loop fasteners, such as Hook-loop fastener, such as Velcro, for fastening the strap to the fabric support 40.

Figure 17:
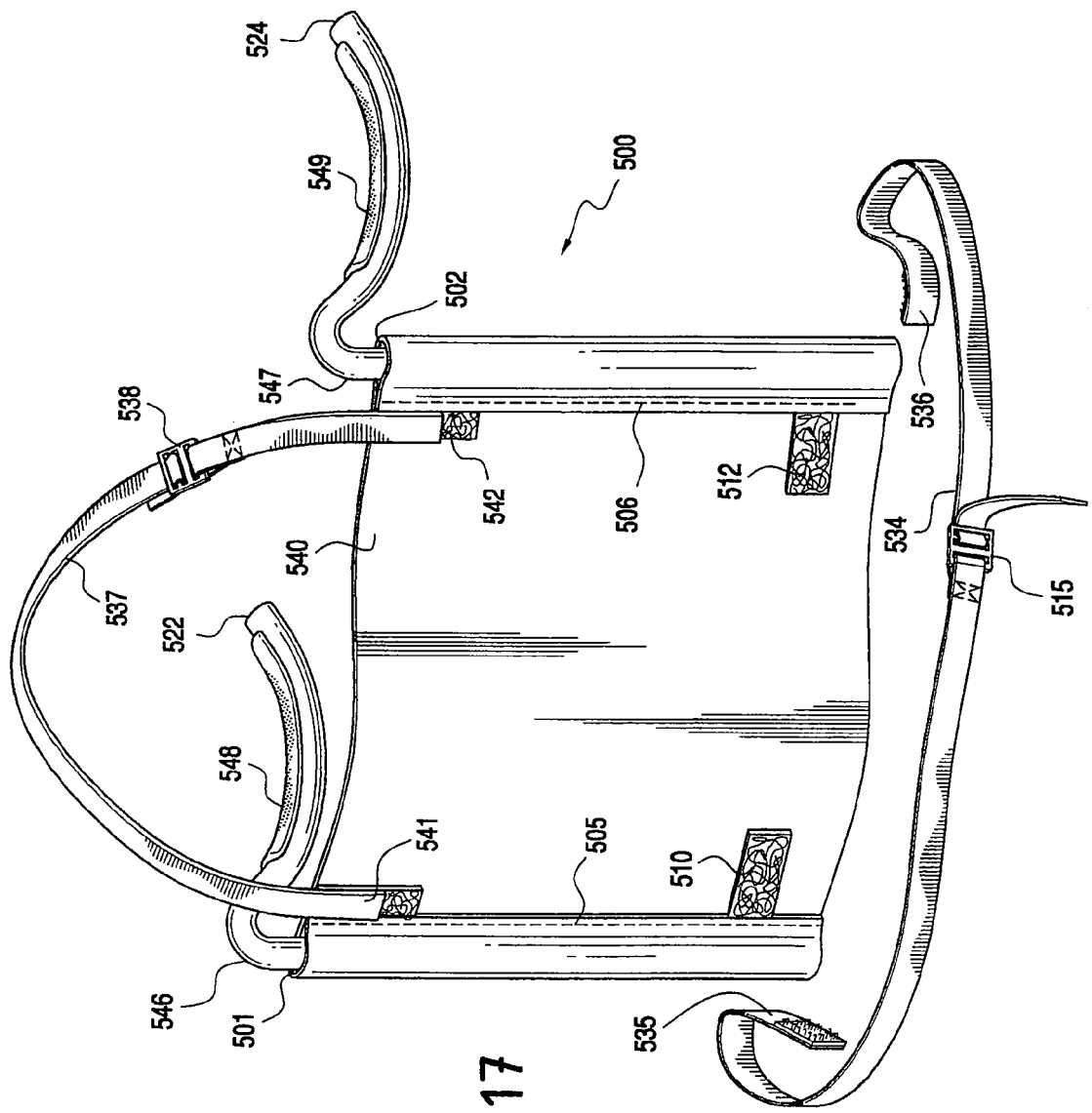
FIG. 17 shows a back perspective view of an alternative embodiment of the present invention.

Referring to FIG. 17, there is illustrated a portable version of my orthopedic back brace 500 comprising a left and a right axilla support member 522, 524, each extending from corresponding vertical left and right support members 546, 547. Preferably, the axilla support 522, 524 and their associated vertical support members 546, 587 are of one piece construction. Flexible fabric cross piece 540 includes channels or sleeves 501, 502 at each end formed by folding the end of the fabric 503, 504 over on itself and stitching the fabric vertically as at 505, 506, represented by the vertical dashes, to provide a vertical channel or sleeve side at each end into which a vertical support member is inserted. Each axillary member 501, 502 is provided with a soft top cushion 548, 549 for comfort when engaged under the arm of the user.

Figure 18:
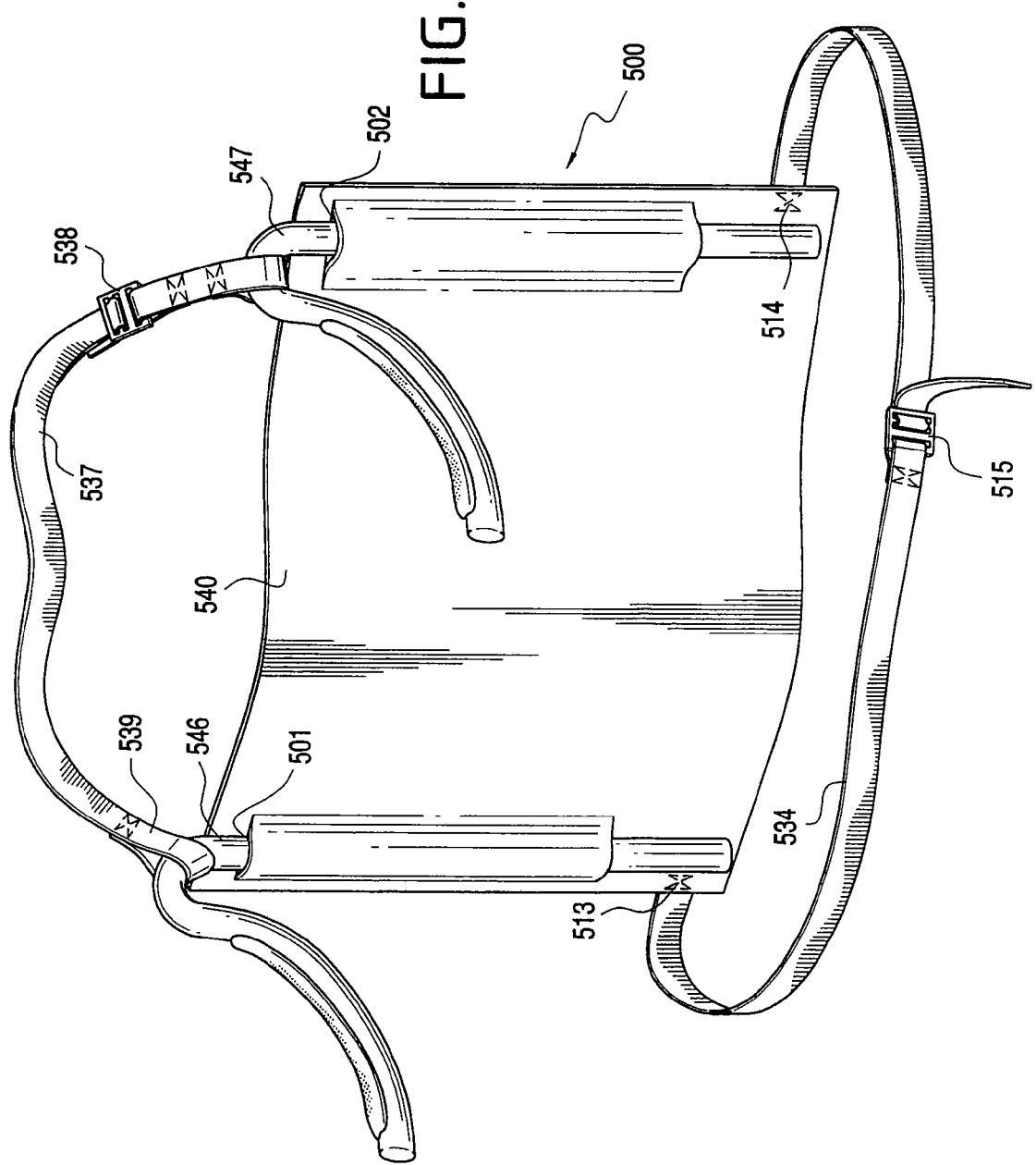
FIG. 18 shows a front perspective view of yet an alternative embodiment of the present invention.

FIG. 18 shows an alternate embodiment of the back brace 500 wherein channels 501, 502 in the back cross piece support fabric are formed by providing upper and lower horizontal slits or openings in the fabric 540 through which the vertical support members 546, 547 pass. A flexible strap 537 is connected at opposite upper ends of the back support. The strap may advantageously include an adjustment buckle 538 as shown in FIGS. 17 and 18 and may be wrapped or looped about the upper ends of the axillary members as at 539. As shown in FIG. 17, opposite ends 541, 542 of flexible strap 537 are provided with hook and loop fasteners, which may be in the form of Hook-loop fastener, such as Velcro straps for attachment of the strap member 537 to the crosspiece fabric 540. Lower stabilizing strap 534 may have at its ends 535, 536 hook and loop fasteners such as Velcro for attachment to fabric 540 at opposite Lower ends 510, 512. Alternatively, the ends of strap 534 may be stitched to the fabric at 513, 514. Buckle 515 allows for adjustment of the strap.

Referring to FIG. 19 there is shown an alternate embodiment of the present invention in which a vehicle seat 600 is retrofitted to receive one-piece axillary support members 601, 602 at opposite sides of back seat 604. Seat 600 includes an upholstered seat back 604, having an inner frame 605, an upper shoulder 606 at each side and a head rest 607. An opening 608 is provided in each shoulder 606 through which the vertical arms 609, 610 of axillary members 601, 602, respectively are inserted.

FIG. 20 shows a section of the seat removed to illustrate connection of the vertical arm to the frame 605. To this end, upper and lower connecting links 615 and 616 are provided between the frame member 605 and vertical arms 609, 610 of the axilla members. Only one axilla arm connection is shown in FIG. 20, it being obvious that a corresponding connection is provided on the other side of seat 604. Links 615, 616 may be conveniently connected at one end to the internal frame 605 by welding, bolts, clamps or the like. The other end of links 615, 616 form a clamp 617, 618 adapted to receive the vertical arm 609 in a manner which allows the arm to rotate along a vertical axis to conveniently position the axilla members out of the way when not in use. In addition to allowing rotation of the axilla vertical arm, the clamping action of link is and as to allow the axilla members to be moved vertically to position the axilla according to the height of the user and to be removed when not in use. A tight friction fit or a pin or peg as 29, 30 such as shown, for example, in FIG. 1 as provided serves this purpose. A plurality of peg holes are arranged vertically in 609. The pin or peg of proper length rests on top of claim 617 allowing vertical adjustment and swiveling.

In retrofitting a vehicle seat, a portion of the seat, usually the top left and right quarter is removed along lines 620 to expose the internal frame 605. This allows insertion of links 615, 616 and clamps 617, 618 on frame 605. Once links 615, 616 and clamps 617, 618 are in place, the removed seat section is restored to its original position. It should also be apparent, that the seat may be fabricated at the manufacturer to include links and clamps for receiving axillary members. If desired, a reinforcement ring 622 may be placed around opening 608 to prevent wear due to frequent insertion of the axillary member.

It should be noted that the orthopedic support seat of FIGS. 19 and 20 provide the desired support for a percentage of the users weight to relieve pressure on the lower back without using a fabric strap behind the head rest. Although, if desired, a strap 537 may be connected to the axillary members 610, 602 for additional support about the head rest as shown for example in FIG. 18. Strap 537 would then be placed about the head rest 607 of the seat. Strap 537 would also serve to keep the axillary members 601, 602 from being pushed too deep into the seat. Head rest 607 is adjustable vertically and may be provided with openings 625 through which a pin 620 may be inserted to allow for vertical adjustment of the axillary members in the manner provided by rod 48 shown in FIG. 21.

Figure 22:
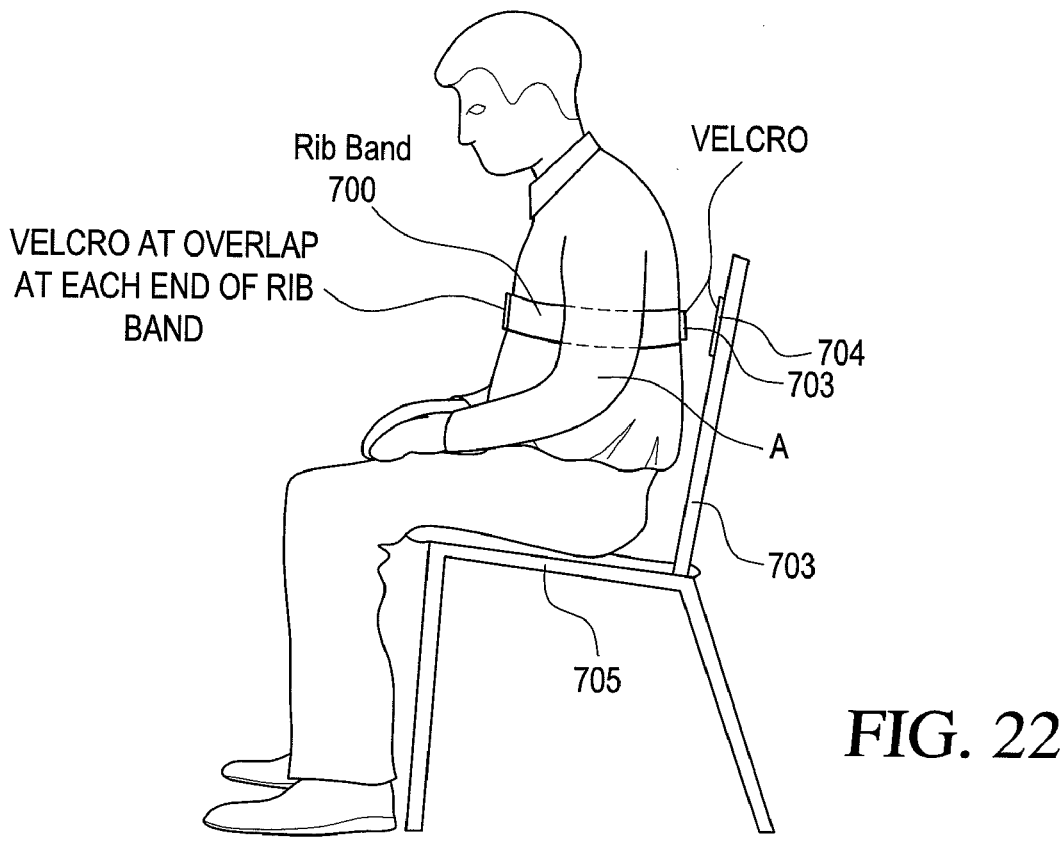
FIG. 22 shows a simplified embodiment of my back support inventions which uses a body or rib band that permits easy ingress and egress from a chair.
Figure 23:
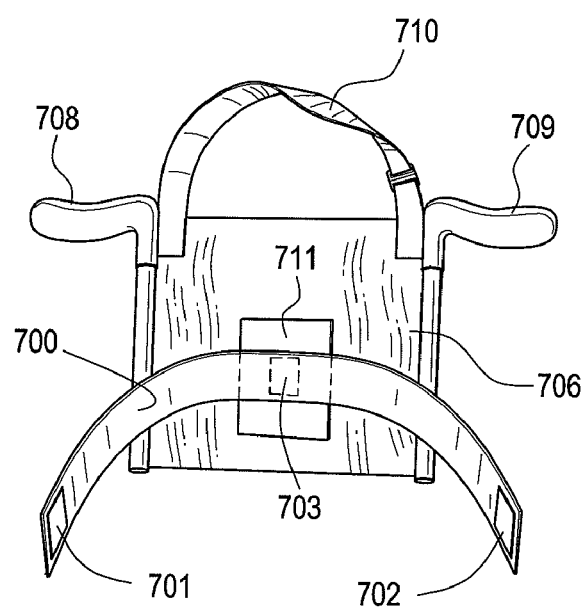
FIG. 23 shows a fragmentary front view of the embodiment shown in FIG. 22.

Referring now to FIGS. 22 and 23, there is shown a simplified version of my orthopedic support having a rib band 700 that wraps around the user's rib cage, just under the arms. It is adjustable at the chest (front) using hook-loop overlap straps 701, 702 such as Velcro or any suitable buckle arrangement. Velcro is a brand name of fabric hook-and-loop fasteners. It consists of two layers: a "hook" side, which is a piece of fabric covered with tiny hooks, and a "loop" side, which is covered with even smaller and "hairier" loops. When the two sides are pressed together, the hooks catch in the loops and hold the pieces together. When the layers are separated, the strips make a characteristic "ripping" sound. The term Velcro is a registered trademark in most countries. Generic terminology for these fasteners includes "hook and loop", "burr" and "touch" fasteners. However the Velcro brand is an example of a genericized trademark as its brand name has become the generic term. The Velcro company headquarters is in Manchester, N.H., USA. The rib band 700 has attached to its back surface a hook type strip 703 which is adapted to connect with a soft loop strip 704 disposed on the front of a seat back 705. The loop strip meshes with this hook strip 703 attached to the back of the rib band 700. By placing the soft looped member on the seat back, the chair can be used without discomfort that might arise if the hooked or rough portion of the Velcro was disposed on the chair to rub on the back of the user.

Vertical lifting or traction is achieved as follows. Prior to the meshing of the strips 703, 704 between the seat-back and the rib band, the user wraps band 700 around the rib cage and under the arm pit cavity and elevates himself slightly above the seat bottom 705 and leans back to mesh the strip attached to the seat-back with the strip attached to the rib wrap. Upon meshing the strips, the rib band will support some weight of the user which is transferred to the seat-back through the hook-loop connection. The meshed strips are strong in shear, but separate easily in tension. This allows the user to move forward horizontally for easy disengagement from the seat back. Disengagement can also be accomplished at the chest by pulling the front strips apart or opening buckle if that is used. There is a choice of disengaging at the chest (front) and leaving the rib band in place attached to the seat-back, or disengaging at the back and leaving the rib band on the body.

The rib band and flexible fabric support member 706 can be used in combination with the back support that uses axillary rests 708 and 709, which are similar to axillary rests 43 and 44, as shown FIG. 5. As noted in the aforenoted previous patents and applications of the inventor, strap 710 is placed about a seat back. It is only necessary to provide a strip attachment member on 711 to the front surface of flexible member 706. If desired a strap 534 may be provided as shown in FIG. 17 to wrap around the seat back 703 to hold the flexible fabric member 706 in place to further cooperate with the strip attachment member 703 on the back surface of rib band 700. In this combination arrangement both the strap 710 positioned behind the seat back and the hook strip on the rib band engaged with the loop strip on the back support work together to transfer weight of the torso to the seat back. To stretch after a period of use, the user need only move forward slightly to break the hook-loop connection.

While this invention has been described in conjunction with specific embodiments thereof, it is evident that many alternatives, modifications and variations will be apparent to those skilled in the art. Accordingly, the preferred embodiments of the invention as set forth herein, are intended to be illustrative, not limiting. Various changes may be made without departing from the true spirit and full scope of the invention as set forth herein and defined in the claims.

What is claimed is:

1. A back support comprising first and second axillary side members, a flexible fabric member disposed between said first and second axillary side members, said flexible fabric member being folded upon itself at each side and vertically stitched to provide a channel at each side for receiving a vertical arm of each of said first and second axillary side members to provide back support for a user, a single upper flexible strap connected at opposite top ends of said flexible fabric member and adapted to be positioned when in use behind a seat back or a head rest of a seat for supporting said flexible fabric member and said axillary side members when in use, and a rib band removably affixed to said flexible fabric member, said flexible fabric member having a first strip on a front surface adapted to attach to a second strip positioned on the back of the rib band disposed about the user, said first and second strips being of a loop and hook fasteners type, said rib band cooperating with the single upper flexible strap, said first and second axillary side members and the flexible fabric member to transfer a weight of a torso of the user to the seat back when in use, and said first strip and said second strip facilitating disengagement of the rib band from the back support when the user moves forward.

2. The back support of claim 1, wherein said rib band has first and second ends adapted to overlap and having third and fourth strips of the hook and loop fastener type at each end to permit adjustment of the rib band to a size of a user and hold a user in place when said first and second strips are engaged.

3. The back support of claim 1 wherein the single upper flexible strap and said flexible fabric member include cooperating hook and loop strips for connecting ends of the upper strap directly to opposite sides of the fabric member.

4. The back support as set forth in claim 3 wherein said single upper flexible strap is adjustable in length.

5. The back support of claim 1 wherein said flexible fabric member and said first and second side members form a collapsible, portable unit.

* * * * *